(12) United States Patent
Whitehead et al.

(10) Patent No.: US 11,291,741 B2
(45) Date of Patent: Apr. 5, 2022

(54) STERTILIZATION POUCH WITH INTERNAL AND EXTERNAL INDICATORS

(71) Applicant: Crosstex International, Inc., Hauppauge, NY (US)

(72) Inventors: Andrew G. Whitehead, Bay Shore, NY (US); Mitchell V. Steinberg, Oyster Bay Cove, NY (US); Charles A. Hughes, Rush, NY (US)

(73) Assignee: Crosstex International, Inc., Hauppauge, NY (US)

( * ) Notice: Subject to any disclaimer, the term of this patent is extended or adjusted under 35 U.S.C. 154(b) by 19 days.

(21) Appl. No.: 16/206,377

(22) Filed: Nov. 30, 2018

(65) Prior Publication Data

US 2019/0091361 A1 Mar. 28, 2019

Related U.S. Application Data

(60) Division of application No. 14/554,928, filed on Nov. 26, 2014, which is a continuation of application No. 12/351,427, filed on Jan. 9, 2009, now abandoned.

(Continued)

(51) Int. Cl.
*A61L 2/28* (2006.01)
*A61L 2/07* (2006.01)
(Continued)

(52) U.S. Cl.
CPC ............... *A61L 2/28* (2013.01); *A61B 50/30* (2016.02); *A61L 2/07* (2013.01); *A61L 2/206* (2013.01);
(Continued)

(58) Field of Classification Search
CPC ... A61L 2/28; A61L 2/206; A61L 2/07; B31B 50/88; B31B 50/74; B31B 50/62;
(Continued)

(56) References Cited

U.S. PATENT DOCUMENTS 2,826,073 A 3/1958 Huyck et al.
3,093,242 A 6/1963 Huyck
(Continued)

OTHER PUBLICATIONS

"Chemical indicators—Guidance for the selection, use, and interpretation of results," Association for the Advancement of Medical Instrumentation, 2000, pp. 1-16.
(Continued)

*Primary Examiner* — Regina M Yoo
(74) *Attorney, Agent, or Firm* — Sorell, Lenna & Schmidt, LLP; William D. Schmidt, Esq.

(57) ABSTRACT

A sterilization package includes a first package layer and a second package layer coupled to the first package layer with a perimeter seal extending around a portion of the sterilization package to define a pouch having a proximal end and a distal end. A first sterilization indicium is disposed on the second package layer exterior of the pouch and a second sterilization indicium is disposed on the second package layer interior of the pouch. The first and second sterilization indicia are multi-parameter sterilization indicia configured to be responsive to a sterilization process such that the first and second sterilization indicia undergo a visual change to a desired ending color when the package is subjected to complete multi-parameter sterilization conditions.

6 Claims, 5 Drawing Sheets

Related U.S. Application Data

(60) Provisional application No. 61/021,104, filed on Jan. 15, 2008.

(51) Int. Cl.
| | | |
|---|---|---|
| *A61L 2/20* | (2006.01) | |
| *B65D 33/00* | (2006.01) | |
| *B65D 33/20* | (2006.01) | |
| *B31B 50/62* | (2017.01) | |
| *B31B 50/74* | (2017.01) | |
| *B31B 50/88* | (2017.01) | |
| *A61B 50/30* | (2016.01) | |

(52) U.S. Cl.
CPC ............. *B31B 50/62* (2017.08); *B31B 50/74* (2017.08); *B31B 50/88* (2017.08); *B65D 33/004* (2013.01); *B65D 33/20* (2013.01); *A61B 2050/314* (2016.02); *B65D 2203/12* (2013.01)

(58) Field of Classification Search
CPC .. A61B 50/30; A61B 2050/314; B65D 33/20; B65D 33/004; B65D 2203/12
See application file for complete search history.

(56) References Cited

U.S. PATENT DOCUMENTS

| | | | |
|---|---|---|---|
| 3,768,725 | A | 10/1973 | Pilaro |
| 3,991,881 | A | 11/1976 | Augurt |
| 4,091,921 | A | 5/1978 | Lewis |
| 4,121,714 | A | 10/1978 | Daly et al. |
| 4,168,779 | A | 9/1979 | Yokokoji et al. |
| 4,177,620 | A * | 12/1979 | Daly ...................... B65B 55/02 426/87 |
| 4,206,844 | A | 6/1980 | Thukamoto et al. |
| 4,358,015 | A | 11/1982 | Hirsch |
| 5,344,017 | A | 9/1994 | Wittrock |
| 5,620,656 | A | 4/1997 | Wensky et al. |
| 6,767,509 | B1 | 7/2004 | Griesbach et al. |
| 2006/0088450 | A1 | 4/2006 | Stecklein |

OTHER PUBLICATIONS

International Standard, ISO 11140-1, 2$^{nd}$ Edition Jul. 15, 2005, Sterilization of Health Care Products—Chemical Indicators—Part 1 General Requirements, pp. 1-27.
International Search Report and Written Opinion for PCT/US2009/030609, dated Apr. 23, 2009, 9 pages.
Medi-Plus® Pre-Folded Self-Seal pouches, website printout, 2 pages.
DUAL Monitor Strip, Product Overview, http://www.spsmedical.com/products . . . , printed Nov. 16, 2007, 4 pages.
STEAM*Plus* Sterilization Integrator, General Information, http://www.spsmedical.com/products . . . , printed Nov. 16, 2007, 1 page.
Technical Bulletin SSI-100, STEAMPlus Sterilization Integrator, from SPS Medical, 2 pages.
ETIGAM brochure, 6 pages.
"Premarket Notification [510(k)] Submissions for Chemical Indicators", Guidance for Industry and FDA Staff; Document issued on: Dec. 19, 2003, 20 pages.
Hi-Performer® Self-Seal pouches, North Bay/Bioscience, LLC, website printout from http://www.nbbs.com/hiperformer.html, printed Nov. 6, 2007, 2 pages.
Crosstex Catalog, Sterilization, pp. 32-33, 2007.
RDH, The National Magazine for Dental Hygiene Professionals, 2 pages, Sep. 2007.
DPREurope.Com, Infection Control Products, pp. 1-2, 2007.
The Dentist Catalogue, Products, Oct. 2007.
Sullivan-Schein Catalog, A Heritage of Service and Innovation, cover page, p. 464, 2007.
ISO 011607-1 European Standard, 2006, Section A.3.3.
3M Attest Products, Sterile U Network Tutorials, Steam Chemical Indicator Classifications, 3 pages, Aug. 1, 2006.
American National Standard, Association for the Advancement of Medical Instrumentation, ANSI/AAMI ST:42:1998, Section 7.4, pp. 18-19.
Appeal Decision of the United States Patent and Trademark Office—Patent Trial and Appeal Board. Appeal No. 2020-000103 filed in corresponding (parent) patent application, U.S. Appl. No. 14/554,928, filed Nov. 26, 2014. Issued Jun. 16, 2021.

* cited by examiner

STERILIZATION POUCH WITH INTERNAL AND EXTERNAL INDICATORS

CROSS-REFERENCE TO RELATED APPLICATIONS

This application is a Continuation of application Ser. No. 12/351,427, filed Jan. 9, 2009, entitled "STERILIZATION POUCH WITH INTERNAL AND EXTERNAL INDICATORS," which claims the benefit of Provisional Application No. 61/021,104, filed Jan. 15, 2008, each of which is incorporated herein by reference in its entirety.

TECHNICAL FIELD

This invention relates to the field of sterilizable packaging using color-changing indicators to display the sterilization status thereof.

BACKGROUND

In the past, packages such as pouches were used to retain contents for medical or veterinary or dental applications and to enable sterilization thereof, with an indication of whether the packaging had undergone sterilization. The two most popular techniques of sterilization for such packages are processing using either steam or ethylene oxide (hereinafter referred to as "ETO").

In the prior art, as discussed in the "BACKGROUND" section of U.S. Pat. No. 4,091,921, it was known to apply indicator ink to the exterior of the package, with a color change indicating that the package was subject to the sterilization process. Different inks were used for steam and ETO as the sterilizing medium. Indicator inks were also applied to the interior of the package, to indicate that the interior sealed chamber containing the contents to be sterilized was subject to at least a partial exposure to a sterilization process. U.S. Pat. Nos. 4,091,921 and 5,344,017 each illustrate a prior art approach in which the indicator ink was sealed in a segregated interior compartment in the pouch to prevent the pouch contents from coming in contact with the interior ink indicator. U.S. Pat. No. 3,093,242 relates to an internal indicator not protected from contact with the contents of the pouch. The entire contents of each of U.S. Pat. Nos. 4,091,921, 5,344,017, and 3,093,242 are expressly incorporated herein by reference.

SUMMARY

In one aspect, the present disclosure relates to a sterilization package including a first package layer and a second package layer coupled to the first package layer with a perimeter seal extending around a portion of the sterilization package to define a pouch having a proximal end and a distal end. The pouch includes a sealable opening at the proximal end. A first sterilization indicium is disposed on the second package layer exterior of the pouch and proximate the distal end of the pouch. A second sterilization indicium is disposed on the second package layer interior of the pouch and proximate the distal end of the pouch. The first and second sterilization indicia are on a side of the second package layer facing the first package layer. The first and second sterilization indicia are multi-parameter sterilization indicia configured to be responsive to a sterilization process such that the first and second sterilization indicia undergo a visual change to a desired ending color when the package is subjected to complete multi-parameter sterilization conditions.

In another aspect, the present disclosure relates to a method for making a sterilization package. A plurality of sterilization indicia are printed on a first major side of a paper layer. The plurality of sterilization indicia include first and second multi-parameter sterilization indicia configured to be responsive to a sterilization process such that the first and second sterilization indicia undergo a visual change to a desired ending color when the package is subjected to complete multi-parameter sterilization conditions. A polymer layer is bonded to the first major side of the paper layer with a perimeter seal. The perimeter seal extends around a portion of the sterilization package to define a pouch having a proximal end with a sealable opening and a distal end. The perimeter seal is disposed between the first and second multi-parameter sterilization indicia at the distal end of the pouch such that the first multi-parameter sterilization indicium is exterior of the pouch and the second multi-parameter sterilization indicium is interior of the pouch.

In a further aspect, the present disclosure relates to a sterilization package including a first package layer and a second package layer coupled to the first package layer with a perimeter seal extending around a portion of the sterilization package to define a pouch having a proximal end and a distal end. The pouch includes a sealable opening at the proximal end. A first steam sterilization indicium is printed on the second package layer exterior of the pouch and proximate the distal end of the pouch. A second steam sterilization indicium is printed on the second package layer interior of the pouch and proximate the distal end of the pouch. The first and second steam sterilization indicia are disposed on a side of the second package layer facing the first package layer. At least one of the first and second steam sterilization indicia is a multi-parameter steam sterilization indicium that is configured to change from a first color to a second color when the sterilization package is subjected to complete sterilization conditions with respect to at least two sterilization process variables selected from the group consisting of time, temperature, and presence of steam.

DETAILED DESCRIPTION

Figure 1:
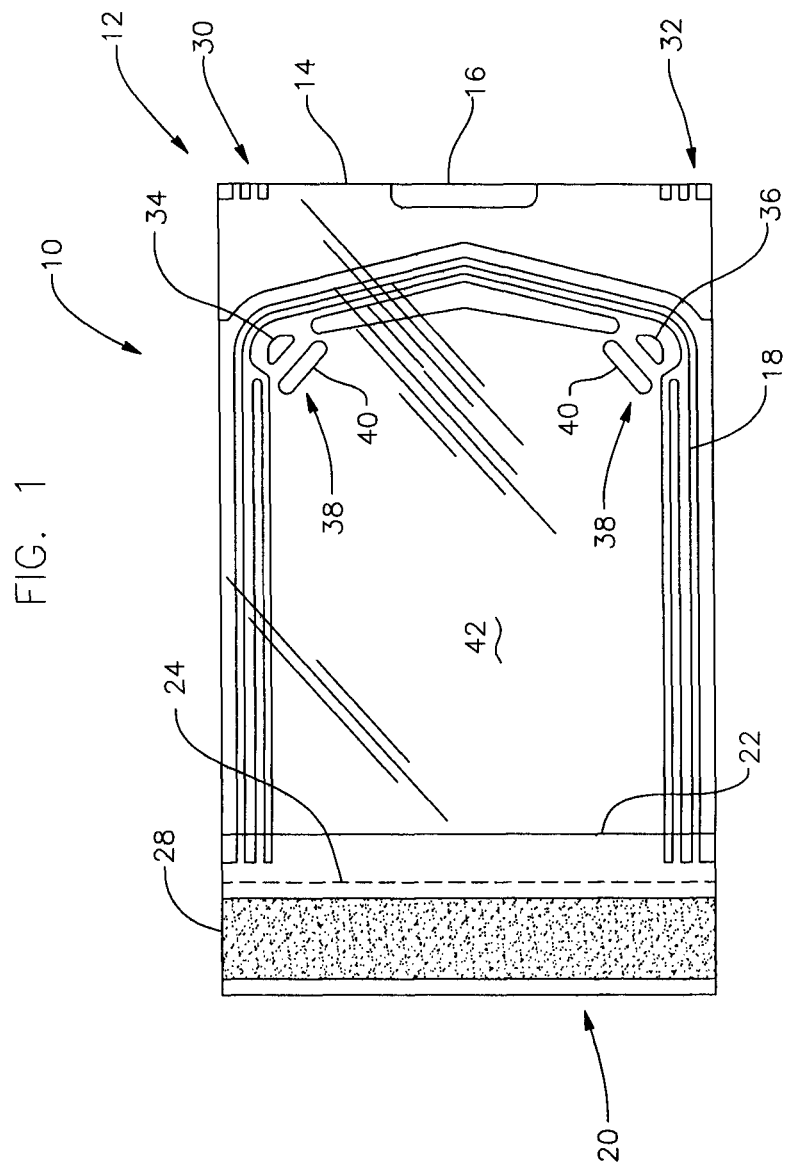
FIG. 1 shows a plan view of a first embodiment of the present invention.
Figure 2:
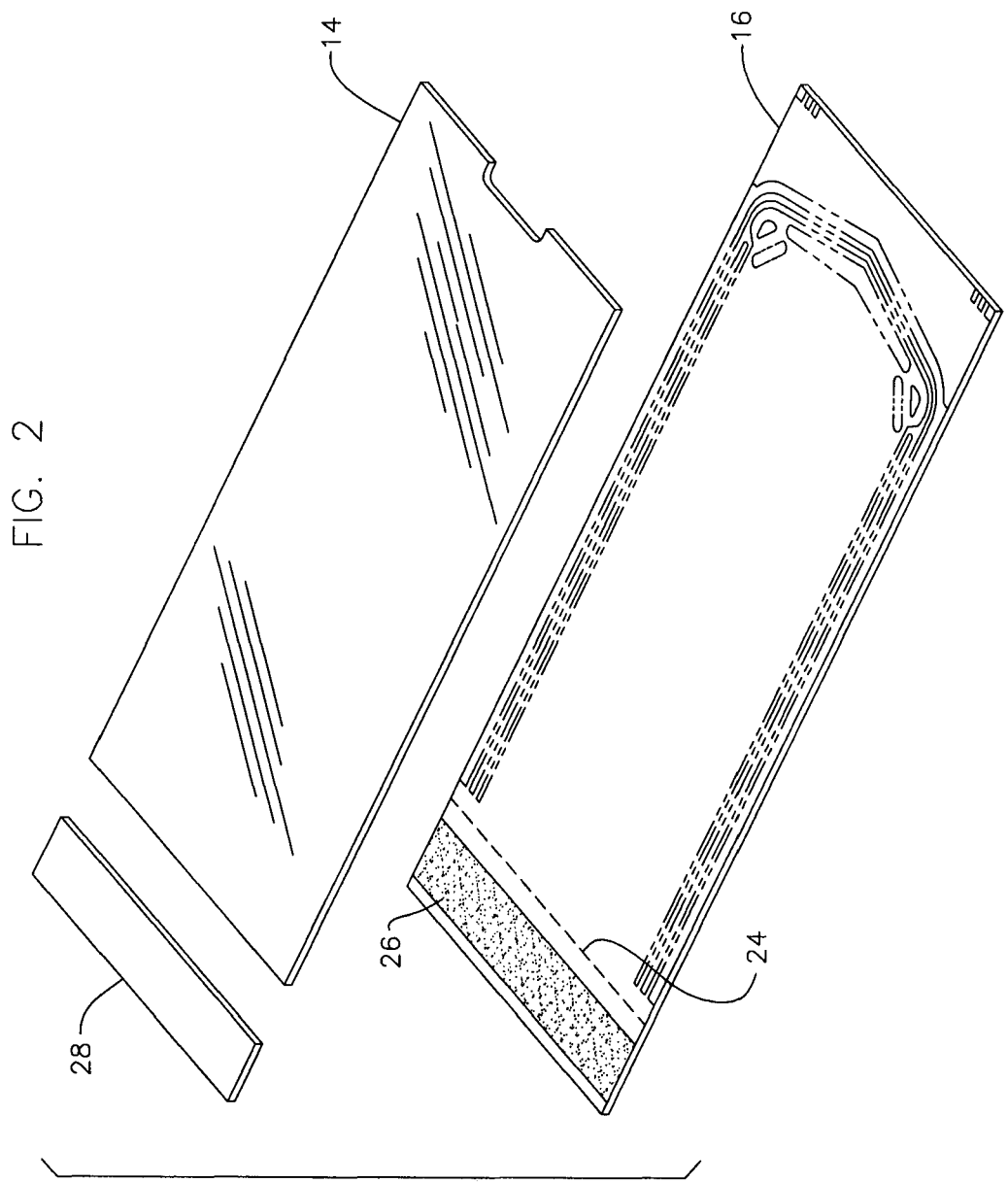
FIG. 2 is an exploded perspective view of the embodiment shown in FIG. 1.

Referring to the Figures and most particularly to FIGS. 1 and 2, a sterilizable package 10 in the form of a pouch 12 useful in the practice of the present invention may be seen. Pouch 12 preferably has a first layer 14 preferably formed of a polyester/polypropylene film bonded to a second layer 16 preferably formed of kraft paper. The bond is formed by a perimeter seal 18 (such as by heat sealing) preferably extending around 3 of the 4 sides of layers 14 and 16 to form the pouch 12 with an initially open end 20, formed by an open edge 22 of the layer 14 not bonded to layer 16. Layer 16 may be perforated along a fold line 24 and preferably has a strip of contact adhesive 26 along open end 20. A release layer 28 initially covers the strip of adhesive 26.

In the practice of the present invention, a pair of first indicia 30, 32 make up the first indicator and are located on the package 10 and exterior of the pouch 12; and a pair of second indicia 34, 36 make up the second indicator and are located on the package 10 and interior of the pouch 12. It is to be understood that the locations of each of the first indicia 30 and 32 may be interchanged; similarly the locations of the second indicia 34 and 36 may be interchanged. As shown, there is one pair of indicia 30, 32 making up the first indicator and another pair of indicia 34, 36 making up the second indicator. One indicium (for example indicium 30) of the first indicator and one indicium (for example indicium 34) of the second indicator may each be responsive to multi-parameter steam sterilization, and the other indicium (for example indicium 32) of the first indicator and the other indicium (for example indicium 36) of the second indicator are each responsive to gas sterilization. The gas is preferably ethylene oxide. The package 10 may thus be seen to include first and second indicators, each of which include a separate indicium for indicating the results of one of steam and gas sterilization, with at least the steam sterilization responsive indicium 34 of the second indicator being a multi-parameter responsive steam sterilization indicium. Preferably both indicia 30 and 34 are responsive to multi-parameter steam sterilization. Each of the indicia 32, 36 may be responsive to multi-parameter gas (such as ethylene oxide) sterilization, as well. Alternatively, the indicia 32 and 36 may undergo a color change simply in response to some exposure to a sterilizing gas medium such as ethylene oxide.

The package 10 may be the same as is used in pouches available from Medi-Plus Laboratories, division of Cur Med Healthcare Packaging of Chicago, Ill., and marketed as a Self-Seal Pouch by Medi-Plus Laboratories. Alternatively, the package 10 may be the same or substantially equivalent to the ProView Sterilization Pouch marketed by Cottrell, Ltd, of Englewood Colo. Neither Medi-Plus nor Cottrell offer pouches that have both process external and multi-parameter internal indicators, however.

The chemical indicators may be in the form of indicia formed by ink printed on one of the layers 14 and 16, preferably layer 16. These indicia undergo a visibly perceptible color change to a desired ending color to indicate that successful sterilization has occurred at the indicator.

Specifically, in one embodiment, the steam sterilization process indicator changes color from one designated initial color (for example, pink) to another, readily distinguishable color (for example, dark brown may be the desired ending color) upon sufficient exposure to complete sterilization conditions (i.e., when exposed to a complete multi-parameter steam sterilization process). The color change to the desired ending color i.e., "designated end color change" may be caused by a chemical reaction in the ink, such as a copper or lead compound reacting with a source of sulfur to produce copper or lead sulfide at the indicia.

Also, in one embodiment, the ETO (ethylene oxide) process indicator changes color from one designated initial color (for example, a blue/grey) to another designated, readily distinguishable color (for example, a gold/brown may be the desired ending color). The color change from blue/grey (as the desired starting color) to gold/brown (as the desired ending color) may be achieved by a pyridine derivative acetylated in a direct reaction with the ETO.

Preferably, the minimum process conditions necessary to cause complete color change (corresponding to "successful sterilization") resulting in achieving the desired ending color in the multi-parameter sterilization process are as follows:

For the steam process sterilization: 10 minutes exposure to steam at 250° F.

For ETO: 60 minutes exposure to ETO at 8 psi and 135° F.

It may be noted that there may be some color change in the steam process indicia with longer periods of exposure below 250° F. or with shorter periods of exposure at temperatures greater than 250° F. Similarly, some color change may be observed for the ETO process indicia with extended exposure at normal room ambient temperatures, and with times as low as 15 minutes with elevated temperature/pressure, and at pressures as low as normal atmospheric ambient pressures with extended time/elevated temperatures. However, when the package or pouch is subjected to only incomplete or insufficient sterilization process conditions in the practice of the present invention, the internal multi-parameter sterilization process indicium will not change to the desired ending color.

In the practice of the present invention, it has been found preferable to include an independent barrier seal 38 in the form of a bar 40 blocking contact by a conventional medical device (not shown) when placed in the interior 42 of the pouch 12 with either of the internal indicators or indicia 34 or 36. Bar 40 is preferably not connected to perimeter seal 18. This has the advantage of preventing contamination of the pouch contents with the ink and also permitting the internal indicators to be in the same compartment as the pouch contents being sterilized. The steam or gas present in the pouch interior 42 is allowed to reach the indicators 34, 36.

To use the package 10 as a pouch for sterilization, contents (such as a medical device) are placed in the pouch interior 42, by insertion past the open edge 22 of the first layer 14. The release layer 28 is then removed, and the second layer 16 is folded along fold line 24 to present adhesive region 26 against the first layer, sealing the open end 20 of the pouch 12.

It is to be understood that the indicators 30 and 32 may be located under respective corners of the first layer 14, however, in the practice of the present invention, the first layer is not secured to the second layer in the corners where indicators 30 and 32 are located, thus presenting indicators to the external environment in which package 10 is located.

Once the package 10 is sealed as described above, it is preferably placed in an appropriate sterilization chamber (not shown) and desirably exposed to the appropriate sterilization process, which may be either steam or gas (such as ETO) at the appropriate conditions and for the appropriate time for that sterilization process.

Both the external and internal indicators undergo a visually perceptible change to the desired ending color when the package is subjected to complete sterilization conditions. However, when steam is the sterilizing medium, only the first (external) indicator may undergo a visually perceptible change to the desired ending color when the package is subjected to an incomplete sterilization conditions. The second (internal) indicator will not undergo a complete color change to the desired ending color in the event the interior 42 of the pouch 12 is not subjected to complete steam sterilization conditions, and thus a color change of the external indicator to the desired ending color without a color change of the internal indicator to the desired ending color will thereafter indicate to a user that steam sterilization was attempted, but was incomplete.

In one aspect, the present invention may thus be seen to be a method of providing a visually perceptible indication of successful or unsuccessful exposure to a proper steam sterilization cycle for the contents of a package of the type having a generally planar polymer layer and a paper member joined together by a marginal seal extending around a portion of a perimeter of the package to form a pouch. The method includes providing the first indicator located on the package and exterior of the pouch; and providing the second indicator located on the package and interior of the pouch.

The method further includes subjecting the package to a steam sterilization process and observing the first and second indicators. In this method, both the first and second indicators undergo a visually perceptible change to a desired ending color when the package is subjected to complete sterilization conditions, but only the first indicator may undergo a visually perceptible change to the desired ending color when the package is subjected to incomplete sterilization conditions. The method includes having the first and second indicators responsive to steam sterilization, and may include indicators responsive to gas sterilization. The method also may include having the first and second indicators each with (separate) indicia responsive to steam or gas sterilization, with the preferred gas being ethylene oxide.

Figure 3:
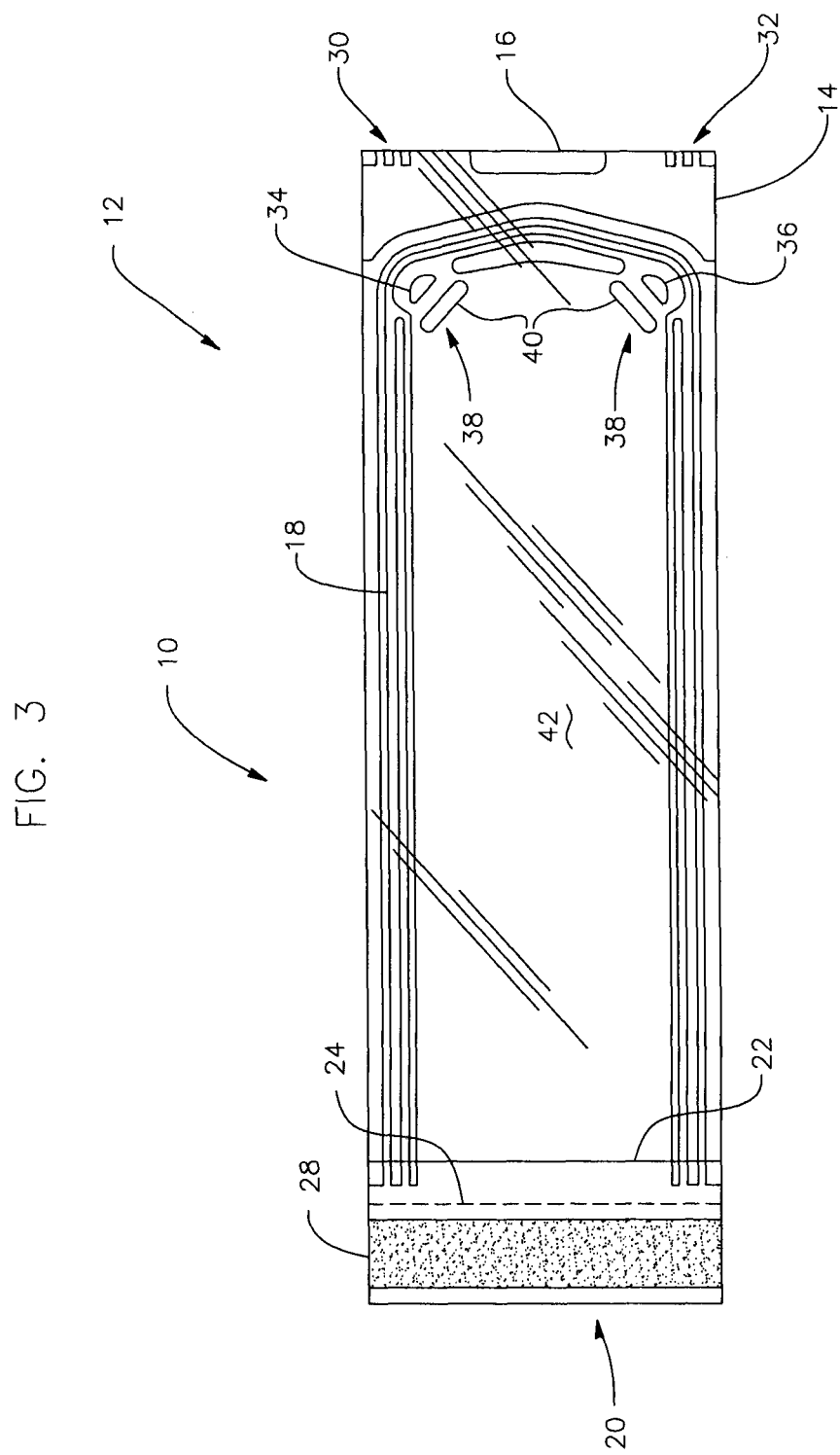
FIG. 3 is a plan view of a second embodiment of the present invention.
Figure 4:
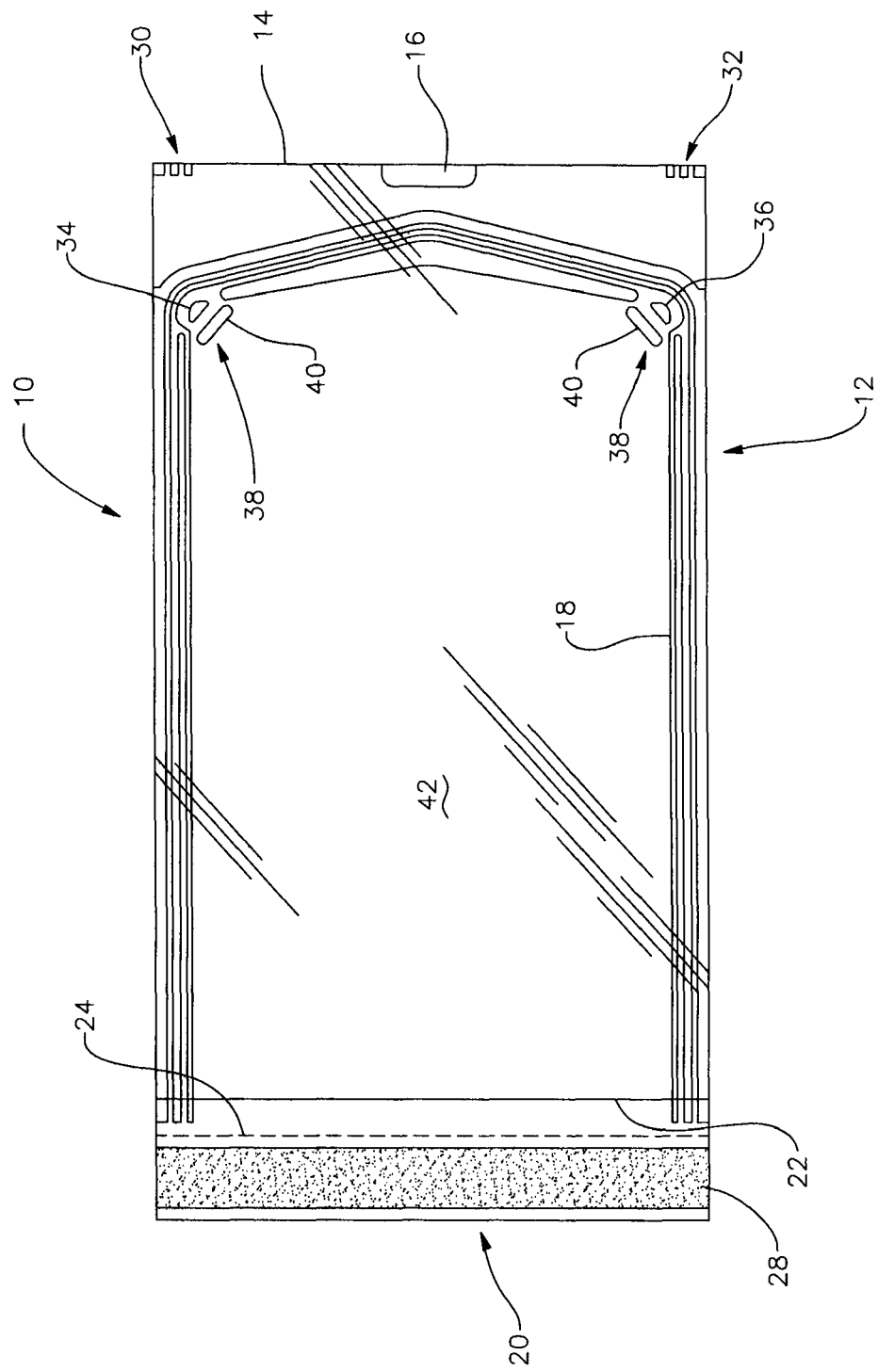
FIG. 4 is a plan view of a third embodiment of the present invention.
Figure 5:
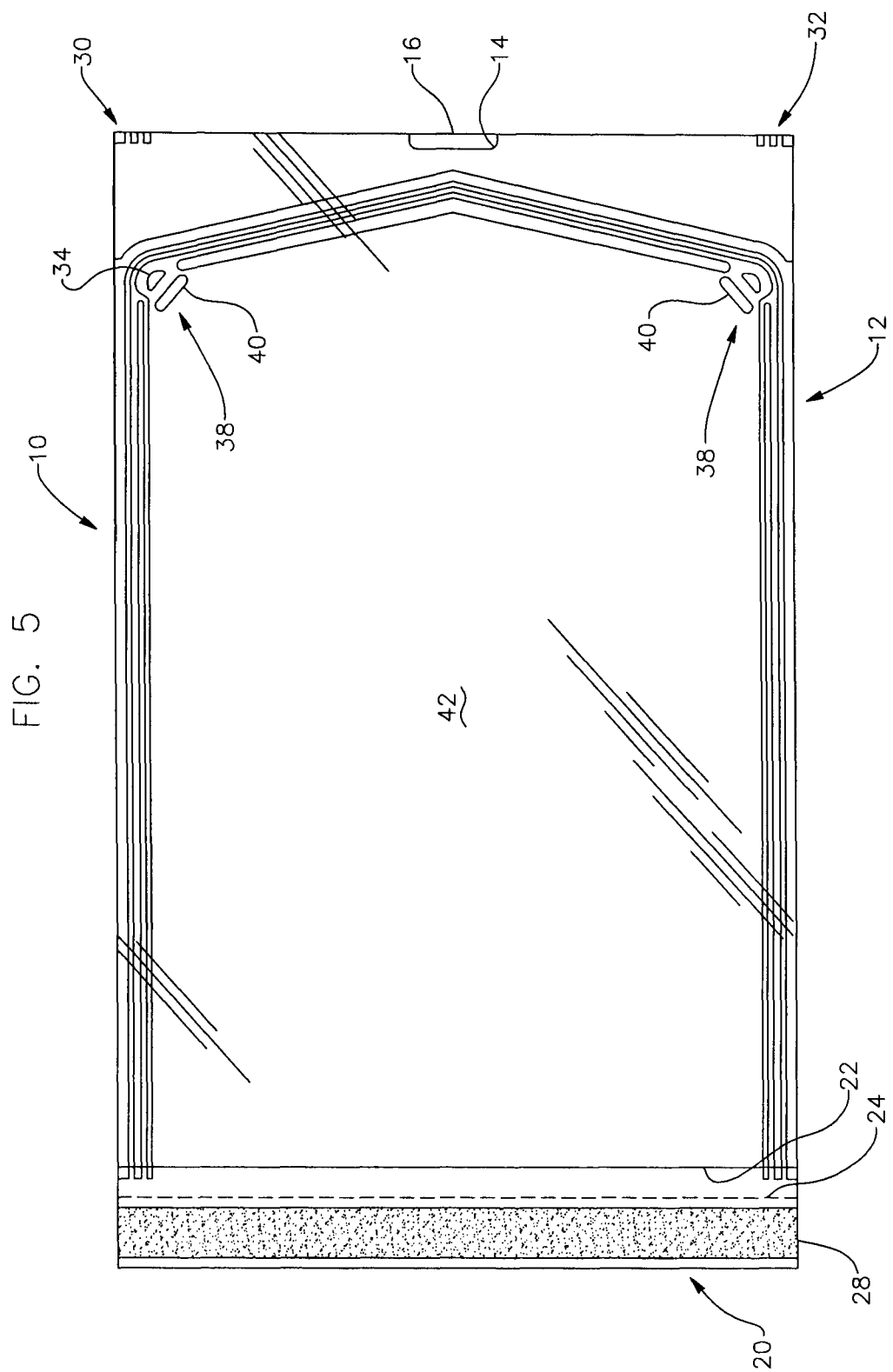
FIG. 5 is a plan view of a fourth embodiment of the present invention.

Examples of other shapes and sizes of pouches useful in the practice of the present invention may be seen in FIGS. 3-5, where like features are numbered the same as in the embodiment shown in FIG. 1. In FIG. 1, the pouch is about 3.5 inches wide by about 5.25 inches in length; the pouch of FIG. 3 is about 2.75 inches wide by about 9 inches in length. The pouch in FIG. 4 is about 5.25 inches wide by about 10.125 inches long. The pouch in FIG. 5 is about 7.5 inches wide by about 13.125 inches long. Dimensions given are for the width of the layers 14 and 16, and lengths are for the length of the first or top layer 14.

The International Organization for Standardization (ISO) is a worldwide federation of national standards entities. ISO/TC 198, Sterilization of Healthcare Products, has developed sterilization standards for medical devices and related healthcare products.

In addition, AAMI standards have been recognized by the United States Food and Drug Administration (FDA). The applicable standard is ANSI/AAMI/ISO 11140-1: 2005, "Sterilization of healthcare products—Chemical Indicators—Part 1: General Requirements" (Arlington, Va.: AAMI, 2005).

Single parameter chemical indicators have been developed to meet the requirements of indicating whether a particular temperature has been reached in a medical device or packaging sterilization process.

In contrast, multi-parameter sterilization chemical indicators respond not only to temperature, but also require sufficient time and/or the presence of sterilizing medium such as steam or ethylene oxide to confirm that sufficient sterilization has been achieved when a medical device package has been subjected to a process intended to sterilize the contents of the package.

The invention may thus be seen to be a sterilizable package comprising a generally planar polymer layer and a paper member joined together by a marginal seal extending around a portion of a perimeter of the package to form a pouch, the package comprising a first indicator located on the package and exterior of the pouch; and a second indicator located on the package and interior of the pouch such that both indicators undergo a visually perceptible change to a desired ending color when the package is subjected to complete multi-parameter steam sterilization conditions, while, at most, only the first indicator will undergo a visually perceptible change to the desired ending color when the package is subjected to incomplete steam sterilization conditions. The first and second indicators include steam sterilization indicators and may include gas sterilization indicators, and the gas may be ethylene oxide. In one embodiment, the first and second indicators may each comprise a separate indicia for indicating one of steam and gas sterilization, again with the gas being ethylene oxide.

The invention may also be characterized as a method of providing a visual indication, such as a color change, of successful or unsuccessful steam sterilization of the contents of a package of the type having a generally non-porous membrane such as a planar polymer layer and a porous membrane such as a paper member joined together by a marginal seal extending around a portion of a perimeter of the package and including an adhesive region on one of the porous and non-porous membranes foldable against the other of the non-porous and porous membranes to form a pouch, with the method comprising providing a first indicator located on the package and exterior of the pouch; and providing a second indicator located on the package and interior of the pouch; subjecting the package to a steam sterilization process; and observing the first and second indicators wherein both the first and second indicators undergo a visual change to a desired ending color when the package is subjected to complete multi-parameter steam sterilization conditions, while, at most, only the first indicator will undergo a visual change to the desired ending color when the package is subjected to incomplete sterilization conditions, as measured multi-parametrically. The method may be further characterized wherein the first and second indicators are responsive to steam sterilization, or to gas sterilization. The method may be further characterized by the first and second indicators each having indicia responsive to steam and gas sterilization. The method may be still further characterized by having the gas be ethylene oxide.

The invention is not to be taken as limited to all of the details thereof, as modifications and variations thereof may be made without departing from the spirit or scope of the invention.

What is claimed is:

1. A method for making a sterilization package, the method comprising: printing a plurality of sterilization indicia on a first major side of a paper layer, the plurality of sterilization indicia including first, second, third and fourth multi-parameter sterilization indicia configured to be responsive to a sterilization process such that the first, second, third and fourth multi-parameter sterilization indicia undergo a visual change to a desired ending color when the sterilization package is subjected to complete multi-parameter sterilization conditions; bonding a polymer layer to the first major side of the paper layer with a perimeter seal, the perimeter seal extending around a portion of the sterilization package to define a pouch having a proximal end with a sealable opening and a distal end; bonding a release layer to the first major side of the paper layer, wherein the perimeter seal is disposed between the first and second multi-parameter sterilization indicia and between the third and fourth multi-parameter sterilization indicia at the distal end of the pouch and the sterilization package includes a first barrier seal and a second barrier seal, the first barrier seal and the second barrier seal disposed adjacent to the second and fourth multi-parameter sterilization indicia respectively, and each barrier seal separated from the perimeter seal.

2. The method of claim 1, wherein the first and the second multi-parameter sterilization indicia are configured to be responsive to a steam sterilization process.

3. The method of claim 1, wherein the third and the fourth multi-parameter sterilization indicia are configured to be responsive to a gas sterilization process.

4. The method of claim 3, wherein the third and the fourth multi-parameter sterilization indicia are configured to be responsive to ethylene oxide.

5. The method of claim 3, wherein the first major side of the paper layer comprises a region configured to bond with the release layer.

6. The method of claim 5, wherein the first major side of the paper layer comprises a fold line separating the region and the perimeter seal.

* * * * *